(12) United States Patent  (10) Patent No.: US 8,857,243 B2
Valenza, II et al.  (45) Date of Patent: Oct. 14, 2014

(54) METHODS OF MEASURING POROSITY ON UNCONVENTIONAL ROCK SAMPLES

(75) Inventors: John J. Valenza, II, Melrose, MA (US); Andrew E. Pomerantz, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 76 days.

(21) Appl. No.: 13/446,995

(22) Filed: Apr. 13, 2012

(65) Prior Publication Data

US 2013/0269420 A1    Oct. 17, 2013

(51) Int. Cl.
*G01N 15/08* (2006.01)

(52) U.S. Cl.
USPC .............................................. 73/38

(58) Field of Classification Search
CPC . G01N 15/08; G01N 15/088; G01N 15/0886; E21B 49/005
USPC ................................. 73/152.07, 38
See application file for complete search history.

(56) References Cited

U.S. PATENT DOCUMENTS

| 4,346,592 | A |   | 8/1982  | Fertl et al. |           |
|-----------|---|---|---------|--------------|-----------|
| 4,594,887 | A |   | 6/1986  | Fertl et al. |           |
| 4,699,002 | A | * | 10/1987 | Rockley      | 73/152.07 |
| 7,511,266 | B1|   | 3/2009  | Bothner      |           |
| 2002/0059028 | A1 |   | 5/2002 | Rozak     |           |
| 2003/0196810 | A1 |   | 10/2003 | Vinegar et al. | |
| 2004/0033557 | A1 |   | 2/2004 | Scott et al. |           |
| 2008/0157584 | A1 |   | 7/2008 | Kieschnick |           |
| 2008/0162056 | A1 |   | 7/2008 | Greaves |           |
| 2009/0254283 | A1 |   | 10/2009 | Jacobi et al. |           |
| 2010/0040281 | A1 | * | 2/2010 | Chen et al. | 382/156 |
| 2010/0058854 | A1 | * | 3/2010 | Waters et al. | 73/152.41 |
| 2010/0185393 | A1 |   | 7/2010 | Liang et al. |           |
| 2010/0256915 | A1 | * | 10/2010 | Frost, Jr. | 702/9 |
| 2011/0068788 | A1 |   | 3/2011 | Minh |           |
| 2011/0282584 | A1 |   | 11/2011 | Baez et al. |           |
| 2012/0192639 | A1 |   | 8/2012 | Valenza, II et al. | |
| 2013/0269933 | A1 |   | 10/2013 | Pomerantz et al. | |

FOREIGN PATENT DOCUMENTS

| EP | 1461821    | 12/2009 |
| WO | 2008082633 | 7/2008  |
| WO | 2008085442 | 7/2008  |
| WO | 2009032924 | 3/2009  |
| WO | 2011085444 | 7/2011  |
| WO | 2011133421 | 10/2011 |

OTHER PUBLICATIONS

Adesida et al., "SPE 147397: Kerogen Pore Size Distribution of Barnett Shale using DFT Analysis and Monte Carlo Simulations," SPE International, 2011: pp. 1-14.
Ambrose et al., "SPE 141416: Multi-component Sorbed-phase Considerations for Shale Gas-in-place Calculations," SPE International, 2011: pp. 1-10.

(Continued)

*Primary Examiner* — Daniel S Larkin
*Assistant Examiner* — Irving A Campbell
(74) *Attorney, Agent, or Firm* — Bridget Laffey; Jakub M. Michna

(57) ABSTRACT

Embodiments disclose methods of estimating porosity from a pore volume and bulk density. The porosity is obtained by multiplying the pore volume and bulk density. Methods disclosed in the subject disclosure are minimally affected by errors in the bulk density measurement.

17 Claims, 2 Drawing Sheets

(56) References Cited

OTHER PUBLICATIONS

Arnarson et al., "Organic-mineral interactions in marine sediments studied using density fractionation and X-ray photoelectron spectroscopy," Organic Geochemistry, 2001, vol. 32: pp. 1401-1415.

Burnham, "Reaction kinetics between CO2 and oil-shale residual carbon. 1. Effect of heating rate on reactivity," Fuel, Apr. 1979, vol. 58: pp. 285-292.

Gale et al., "Effects of Pyrolysis Conditions on Internal Surface Areas and Densities of coal Chars Prepared at High Heating Rates in Reactive and Nonreactive Atmospheres," Energy & Fuels, 1995, vol. 9: pp. 513-524.

Yu et al., "The Role of Clay Minerals in the Preservation of Organic Matter in Sediments of Qinghai Lake, NW China," Clays and Clay Minerals, 2009, vol. 57(2): pp. 213-226.

Hartman et al., "SPE 144097: Shale Gas-in-Place Calculations Part II—Multi-component Gas Adsorption Effects," SPE International, 2011: pp. 1-17.

Hedges et al., "Sedimentary organic matter preservation: an assessment and speculative synthesis," Marine Chemistry, 1995, vol. 49: pp. 81-115.

Hildenbrand et al., "Gas breakthrough experiments on fine-grained sedimentary rocks," Geofluids, 2002, vol. 2: pp. 3-23.

Keil et al., "Loss of organic matter from riverine particles in deltas," Geochimica et Cosmochimica Acta, 1997, vol. 61 (7): pp. 1507-1511.

Kennedy et al., "Mineral Surface Control of Organic Carbon in Black Shale," Science, Jan. 2002. vol. 295: pp. 657-660.

Kline et al., "Dissolution of Silicate Minerals by Hydrofluoric Acid," Ind. Eng. Chem. Fundam., 1981, vol. 20(2): pp. 155-161.

Klinkenberg, "The Permeability of Porous Media to Liquids and Gases," Production Practice, 1941: pp. 200-213.

Kulaots et al., "Characterization of Chinese, American and Estonian oil shale semicokes and their sorptive potential," Fuel, 2010, vol. 89: pp. 3300-3306.

Mayer, "Relationships between mineral surfaces and organic carbon concentrations in soils and sediments," Chemical Geology, 1994, vol. 114: pp. 347-363.

Mayer, "Extent of coverage of mineral surfaces by organic matter in marine sediments," Geochimica et Cosmochimica Acta, 1999, vol. 63(2): pp. 207-215.

Mayer et al., "Organic matter in small mesopores in sediments and soils," Geochimica et Cosmochimica Acta, 2004, vol. 68(19): pp. 3863-3872.

Oya et al., "Porous structure of residue (spent shale) from oil shale," Journal of Materials Science, 1990, vol. 25: pp. 879-885.

Perez et al., "Dissolved organic matter dynamic in the Amazon basin: Sorption by mineral surfaces," Chemical Geology, 2011, Vol. 286: pp. 158-168.

Pugh et al., "Pyrite and Marcasite Surface Area as Influenced by Morphology and Particle Diameter," Soil Sci. Soc. Am. J., 1981, vol. 45: pp. 979-982.

Qing et al., "Variation of the Pore Structure During Microwave Pyrolysis of Oil Shale," Oil Shale, 2010, vol. 27(2): pp. 135-146.

Qing et al., "The Influence of Microwave Drying on Physicochemical Properties of Liushuhe Oil Shale," Oil Shale, 2011, vol. 28(1): pp. 29-41.

Ransom et al., "TEM study of in situ organic matter on continental margins: occurrence and the 'monolayer' hypothesis," Marine Geology, 1997, vol. 138: pp. 1-9.

Ransom et al., "Organic matter preservation on continental slopes: Importance of mineralogy and surface area," Geochimica et Cosmochimica Acta, 1998, vol. 62(8): pp. 1329-1345.

Ross et al., "The importance of shale composition and pore structure upon gas storage potential of shale gas reservoirs," Marine and Petroleum Geology, 2009, vol. 26: pp. 916-927.

Valenza, et al., "Geochemical Controls on Gas Shale Reservoir Quality", AAPG Search and Discovery, Dec. 2010, 1 page.

Yee, et al., "Gas Sorption on Coal and Measurement of Gas Content", Chapter 9, AAPG Special Volumes, vol. SG 38: Hydrocarbons from Coal, 1993, pp. 203-218.

Loermans et al., "Results from pilot tests prove the potential of Advanced Mud Logging", SPE 149134, presented at the SPE/DGS Saudi Arabia Section Technical Symposium and Exhibition held in Al-Khobar, Saudi Arabia, May 15-18, 2011, pp. 1-9.

International Search Report and Written Opinion issued in PCT/US2012/022975 on Aug. 28, 2012, 13 pages.

International Search Report and Written Opinion issued in PCT/US2013/034777 Sep. 17, 2013, 9 pages.

\* cited by examiner

METHODS OF MEASURING POROSITY ON UNCONVENTIONAL ROCK SAMPLES

FIELD

This disclosed subject matter is generally related to gas shale formations, and more particularly to methods for measuring the porosity of a rock sample from an unconventional hydrocarbon reservoir.

BACKGROUND

Multiple methods exist for measuring porosity. A common method for measuring porosity is to calculate porosity from measurements of both bulk density, also referred to as envelope density, and skeletal density, also referred to as grain density. This technique is commonly used in laboratory core analysis, bulk density measured by caliper and skeletal density measured by pycnometry; and in downhole logging, bulk density measured by a density tool and skeletal density assumed or estimated from mineralogy. Porosity is also commonly measured downhole with a neutron tool. Finally, porosity may be measured by nuclear magnetic resonance (NMR) both downhole, for example with the Schlumberger's Combinable Magnetic Resonance Tool (CMR tool), and on cores or cuttings.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method of calculating porosity of a rock sample from an unconventional hydrocarbon reservoir is disclosed. The method comprises measuring a pore volume of the rock sample from the unconventional hydrocarbon reservoir, measuring a bulk density of the rock sample from the unconventional hydrocarbon reservoir; and computing a porosity of the rock sample by multiplying the measured bulk density by the measured pore volume.

According to some other embodiments, a computer program comprising machine readable instructions stored on machine readable media, the instructions for calculating porosity of a rock sample from an unconventional hydrocarbon reservoir. The instructions include receiving input data comprising a pore volume and a bulk density; and computing a porosity of the rock sample by multiplying the bulk density by the measured pore volume.

As used herein the term "unconventional" reservoir includes reservoirs having an unconventional microstructure, such as having submicron pore size, and/or substantial amounts of primary organic matter such as kerogen.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicate like elements.

In embodiments, methods are disclosed for estimating porosity of cuttings from gas shales and oil-bearing shales. The methods disclosed may also be applied to cores.

Figure 1:
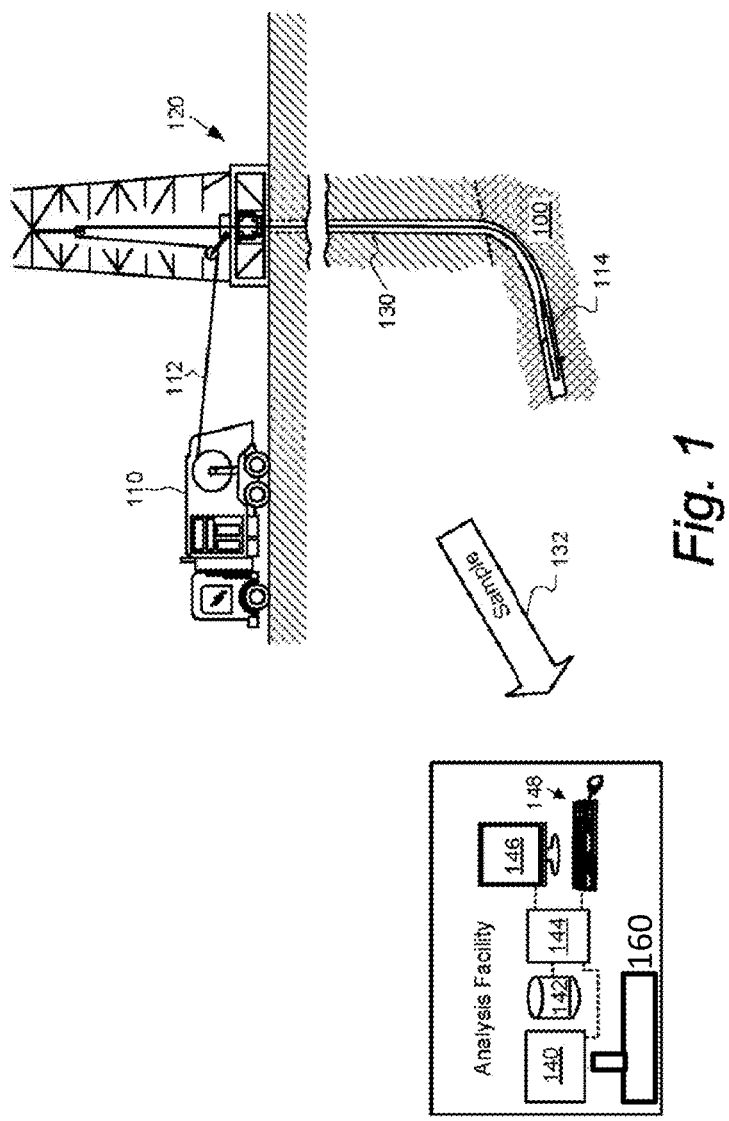
FIG. 1 shows a sampling tool being deployed in a wellbore and an analysis facility, according to some embodiments.

FIG. 1 shows a sampling tool being deployed in a wellbore and an analysis facility, according to some embodiments. In a non-limiting example the sampling tool is a core sampling tool. Wireline truck 110 is deploying wireline cable 112 into well 130 via well head 120. Wireline tool 114 is disposed on the end of the cable 112 in an unconventional subterranean formation 100. According to some embodiments, formation 100 is an unconventional reservoir, such as a hydrocarbon bearing shale reservoir. Tool 114 includes a sampling tool as shown, in a non-limiting example a core sampling tool. Although a wireline sampling tool is shown, according to other embodiments, other types of sampling tools are used such as while drilling and/or coiled tubing conveyed tools. Samples 132 are from an unconventional rock formation 100 and are retrieved at the surface from the tool 114 and transported to an analysis facility 160. In non-limiting examples, the samples may include cores or cuttings. Note that the analysis facility 160 can be located at the wellsite (which can be onshore or offshore) or it can be located remotely from the wellsite. Facility 160 includes one or more central processing units 140, storage system 142, communications and input/output modules 144, a user display 146 and a user input system 148. Facility 160 may also include a gas sorption apparatus, helium pycnometry (He-pyc), mercury intrusion porosimetry (MICP), bulk density analyzer, grain density analyzer, or other apparatuses as known to those skilled in the art for characterizing rock samples.

Embodiments disclose methods of estimating porosity. In embodiments, the methods of estimating porosity rely on measuring the pore volume and bulk density. The porosity is then determined by multiplying pore volume and bulk density. In situations where the rock sample is cuttings the measurements are performed after cleaning the cuttings. Methods disclosed are minimally affected by errors in the bulk density measurements.

The following definitions are used in the specification:
$\phi$=porosity, unitless
PV=pore volume, cc/g, which is the volume of the sample occupied by pores, normalized by the mass of the sample and may be measured by gas sorption, or mercury intrusion.
$\rho_g$=grain density, g/cc $\rho_b$=bulk density, g/cc—This bulk density is recorded with the pores empty, as opposed to the log bulk density which is measured with the pores saturated with fluid
$m_s$=mass of solids, g
$V_s$=volume of solids, cc
$V_p$=volume of pores, cc $$\varphi \equiv \frac{V_p}{V_p + V_s}$$

$$\rho_g \equiv \frac{m_s}{V_s}$$

$$\rho_b \equiv \frac{m_s}{V_p + V_s}$$

$$PV \equiv \frac{V_p}{m_s}$$

In embodiments, the equation used to estimate porosity is as follows:

$$\varphi = PV \times \rho_b \quad \text{Equation 1}$$

Equation 1 can be proved using:

$$PV \times \rho_b = \frac{V_p}{m_s} \times \frac{m_s}{V_p + V_s} = \frac{V_p}{V_p + V_s} = \varphi$$

Figure 2:
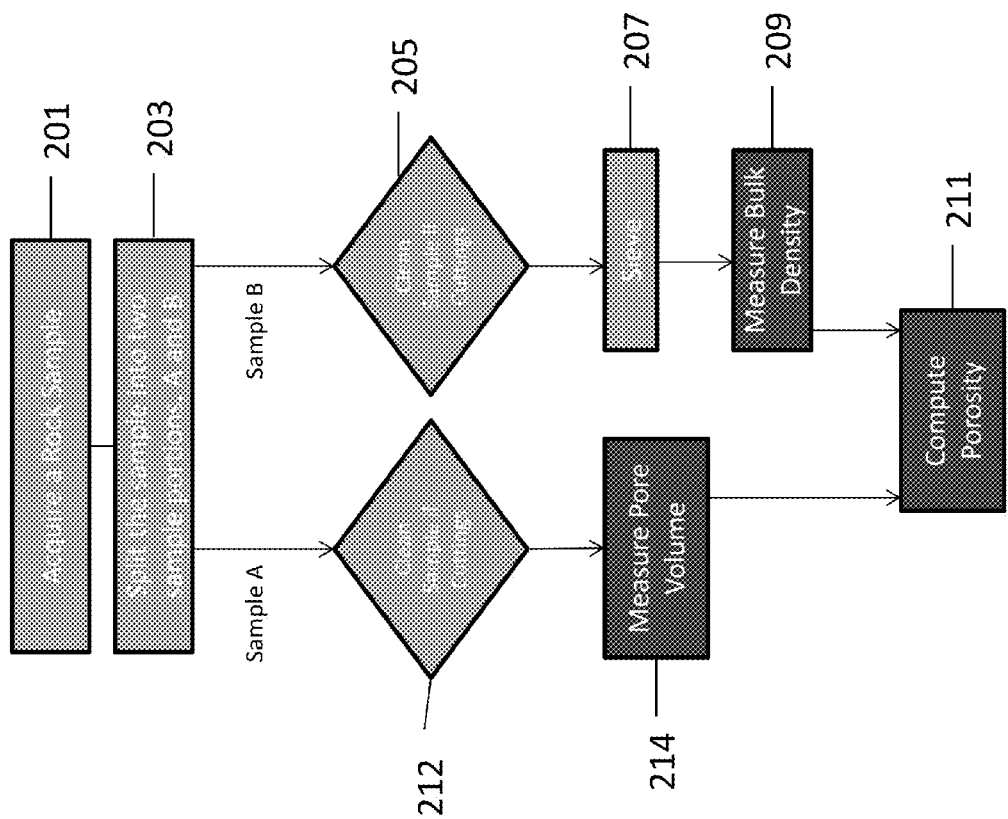
FIG. 2 is a flow chart of an embodiment of the subject disclosure.

FIG. 2 depicts a flow chart of embodiments of the subject disclosure. In embodiments a rock sample is acquired (201) from an unconventional rock formation using any of the known methods for obtaining a rock sample. The rock sample obtained may be core samples drilled from the rock or alternatively cuttings produced while drilling a well.

The rock sample (201) is then split into a first and a second sample (203), depicted in FIG. 2 as sample A and sample B. For a drill cuttings sample for a well drilled with an oil-based mud the first sample (212) is cleaned using the techniques disclosed in co-owned United States patent application Serial No. entitled "Method and Apparatus to Prepare Drill Cuttings for Petrophysical Analysis by Infrared Spectroscopy and Gas Sorption," filed Apr. 13, 2012; the contents of which are herein incorporated by reference. If a water-based mud is used the sample may be cleaned using any of the known techniques for cleaning samples from a well drilled with a water-based mud.

The pore volume (214) may then be determined using helium pycnometry (He-pyc), mercury intrusion porosimetry (MICP) or gas sorption, as independent or complimentary measurements. These techniques are disclosed in commonly co-owned U.S. patent application Ser. No. 13/359,121 filed on Jan. 26, 2012, which is incorporated herein by reference. Other techniques known to those skilled in the art for measuring the pore volume may also be used.

If sample B is a drill cuttings sample from a well drilled with an oil-based mud, the sample is cleaned (205) by rinsing with base oil over a sieve to remove mud additives and then rinsed a second time to remove the residual base oil. It is important to not crush the sample. The goal of cleaning the drill cuttings sample is to remove additives and base oil without altering the drill cuttings or reducing the particle size. It is not necessary to clean sample B completely as an advantage of the subject disclosure is the reduction in sensitivity to errors in the bulk density measurement. The second rinse may involve solvent extraction at elevated temperature and pressure, for example using a SpeedExtractor by Buchi, or other similar instruments as known to those in the art. However, solvent extraction at elevated temperature and pressure is beneficial but may not be required. Alternatively, the second rinse may involve simple rinsing with a volatile solvent such as pentane or similar solvents, as known to those in the art.

The second sample may be sieved (207) to discard the fraction with particle sizes which are not appropriate for a particular bulk density measurement, in a non-limiting example, the particle sizes which are discarded are below 2 millimeters. This size is larger than the representative elemental volume of typical shales, so the sieving process will not bias the sample. The bulk density of the sample is measured using any conventional technique, in a non-limiting example, the GeoPyc 1360 Envelope Density Analyzer by Micromeritics. Step (207) may not be necessary in certain situations, but in other situations it may increase the accuracy of the bulk density measurements. With measured values of pore volume and bulk density, the porosity (211) is then computed using equation 1 above.

Methods disclosed are relatively insensitive to errors in the bulk density measurements. This is an important feature because bulk density, in general, is difficult to measure accurately for unconventional rocks, particularly cuttings from unconventional rocks that need to be cleaned prior to analysis. Accurate bulk density measurement is difficult because the measurement requires larger particles that are free from contamination from drilling fluid. Cleaning cuttings without reducing their particle size may be difficult. Hence, errors in bulk density are expected, and a method of estimating porosity that is minimally impacted by errors in bulk density measurement is desirable.

Embodiments disclosed are less sensitive to errors in bulk density than the more common methods involving bulk density and grain density. The reasons for this decrease in sensitivity will now be explained.

For a shale, typical vales for PV, $\rho_b$, $\rho_g$ are as follows: PV values are typically around 0.04 cc/g, although it can vary over a large range, perhaps 0.01-0.10 cc/g; $\rho_b$ is typically around 2.2 g/cc, and it typically varies over a small range, perhaps 2.0-2.5 g/cc; $\rho_g$ is slightly larger, typically around 2.4 g/cc, and it also varies over a small range, perhaps 2.2-2.6 g/cc. The common method for estimating porosity from bulk density and grain density involve the equation $$\varphi = 1 - \frac{\rho_b}{\rho_g}.$$

These two densities are comparable and vary over small ranges. This means that a large change in porosity will create a small difference between grain density and bulk density. Thus, a small experimental error in bulk density will appear as a large change in porosity. For example, take a rock with a grain density of 2.4 g/cc and a bulk density of 2.2 g/cc. The porosity from these measurements is computed and then the porosity is computed if the bulk density were measured at 2.1 g/cc due to experimental error:

| Grain density (g/cc) | Bulk density (g/cc) | Porosity (pu) |
|---|---|---|
| 2.4 | 2.2 | 8.3 |
| 2.4 | 2.1 | 12.5 |

A small error in bulk density (0.1 g/cc) leads to a large error in porosity (4.2 pu) which is unacceptable for shales.

In equation 1 above, porosity is determined by multiplying pore volume by bulk density; and bulk density varies over a small range and pore volume varies over a large range. Therefore, the porosity information is typically controlled by the pore volume measurement, and small errors in bulk density will lead to small errors in porosity. For example, if we take the same rock as above, which we assume has a pore volume of 0.04 cc/g and compute how much this same variation in bulk density will affect the computed porosity:

| Pore Volume (cc/g) | Bulk density (g/cc) | porosity (pu) |
|---|---|---|
| 0.04 | 2.2 | 8.8 |
| 0.04 | 2.1 | 8.4 |

As can be seen this small error in bulk density (0.1 g/cc) leads to a small error in porosity (0.4 pu). A measurement of (0.4 pu) is negligible for shales. The error in porosity obtained using this equation will also depend on errors in pore volume measurements, but as disclosed in commonly co-owned U.S. patent application Ser. No. 13/359,121 filed on Jan. 26, 2012, which is incorporated herein by reference, pore volume can be measured accurately as it can be measured on small particles.

Embodiments of the subject disclosure may be used for geo-steering. The technique of directional drilling using a formation property measurement as a guide to trajectory adjustment is generally referred to as "geo-steering."

Although only a few example embodiments have been described in detail above, those skilled in the art will readily appreciate that many modifications are possible in the example embodiments without materially departing from methods to measure porosity on unconventional rock samples. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of calculating porosity of a rock sample from an unconventional hydrocarbon reservoir comprising:
    measuring a pore volume of the rock sample from the unconventional hydrocarbon reservoir using a device selected from the group consisting of gas sorption, pycnometry or mercury intrusion porosimetry, or combinations thereof;
    measuring a bulk density of the rock sample from the unconventional hydrocarbon reservoir using a density measuring device; and
    using a processor to compute a porosity of the rock sample wherein the porosity is obtained by multiplying the measured bulk density by the measured pore volume.

2. The method of claim 1, wherein the sample is a cutting sample from the unconventional hydrocarbon reservoir.

3. The method of claim 2, further comprising:
    cleaning the cutting sample to remove drilling mud and oil.

4. The method of claim 3, wherein cleaning the cutting sample uses a solvent extraction at an elevated temperature and pressure.

5. The method of claim 1, wherein the method decreases sensitivity to measured bulk density errors.

6. The method of claim 1, wherein the rock sample is divided into a first sample and a second sample.

7. The method of claim 6, wherein measuring the pore volume comprises measuring the pore volume of the first sample.

8. The method of claim 6, wherein measuring the bulk density comprises measuring the bulk density of the second sample.

9. The method of claim 8, further comprising:
    sieving the second sample to selectively retain particles having a size suitable for measuring the bulk density.

10. The method of claim 1, wherein the unconventional hydrocarbon reservoir includes hydrocarbon-bearing shales.

11. The method of claim 1, wherein the method is performed at a well site.

12. The method of claim 1, wherein the method is performed at a location remote from a well site.

13. The method of claim 1, further comprising:
    using the computed porosity for a geosteering system.

14. A computer program comprising non-transitory machine readable instructions stored on machine readable media, the instructions for calculating porosity of a rock sample from an unconventional hydrocarbon reservoir comprising:
    receiving input data comprising a pore volume and a bulk density; and
    computing a porosity of the rock sample by multiplying the bulk density by the measured pore volume.

15. The computer program of claim 14, wherein the program decreases sensitivity to measured bulk density errors.

16. The computer program of claim 14, wherein the program is included in reservoir characterization of a wellbore.

17. The computer program of claim 14, wherein the program is included in a hydrocarbon recovery process.

* * * * *